(12) United States Patent
Wei (10) Patent No.: US 9,119,726 B2
(45) Date of Patent: Sep. 1, 2015

(54) EXPANDABLE IMPLANT OF A MINIMALLY INVASIVE SURGERY

(71) Applicant: Chih-Hsuan Wei, Chiayi (TW)

(72) Inventor: Chih-Hsuan Wei, Chiayi (TW)

( * ) Notice: Subject to any disclaimer, the term of this patent is extended or adjusted under 35 U.S.C. 154(b) by 155 days.

(21) Appl. No.: 13/845,235

(22) Filed: Mar. 18, 2013

(65) Prior Publication Data

US 2014/0277492 A1    Sep. 18, 2014

(51) Int. Cl.
  *A61F 2/44*    (2006.01)
  *A61F 2/30*    (2006.01)

(52) U.S. Cl.
  CPC .............. *A61F 2/442* (2013.01); *A61F 2/4455* (2013.01); *A61F 2002/30176* (2013.01); *A61F 2002/30471* (2013.01); *A61F 2002/30556* (2013.01); *A61F 2002/30579* (2013.01); *A61F 2002/30891* (2013.01)

(58) Field of Classification Search
  CPC .................. A61F 2/442; A61F 2/4455; A61F 2002/30471; A61F 2002/30556; A61F 2002/30579
  USPC .................................. 623/17.11, 17.15, 17.16
  See application file for complete search history.

(56) References Cited

U.S. PATENT DOCUMENTS

| 8,628,577 | B1* | 1/2014 | Jimenez | 623/17.15 |
| 2008/0114367 | A1* | 5/2008 | Meyer | 606/90 |
| 2008/0147193 | A1* | 6/2008 | Matthis et al. | 623/17.16 |

* cited by examiner

*Primary Examiner* — Jerry Cumberledge
*Assistant Examiner* — Nicholas Plionis
(74) *Attorney, Agent, or Firm* — Alan D. Kamrath; Kamrath IP Lawfirm, P.A.

(57) ABSTRACT

An expandable implant of a minimally invasive surgery contains a body, a positioning post, two first connecting sets, two second connecting sets, and two expanding pieces. The body includes two seats and an adjusting knob. The positioning post inserts into the body and includes one side contacting with the adjusting knob and another side having a conical member. The two first connecting sets couple with the two seats, and each first connecting set has two first rods coupling with a respective one of the two seats. The two second connecting sets connects with the positioning post, and each second connecting set has two second rods coupling with the positioning post. Each expanding piece axially connects with one of the two first rods of each first connecting set and one of the two second rods of each second connecting set.

4 Claims, 8 Drawing Sheets

EXPANDABLE IMPLANT OF A MINIMALLY INVASIVE SURGERY

BACKGROUND OF THE INVENTION

1. Field of the Invention

The present invention relates to an expandable implant of a minimally invasive surgery which has a symmetrical connecting structure to generate an expansion and to retain a bottom end of two sides of an implanted portion, treating and rectifying bone tissue and structure.

2. Description of the Prior Art

A conventional expandable implanting device has a threaded driving structure, but the threaded driving structure cannot expand spines quickly, and a gap is generated in a threaded transmitting process, thus causing operation imbalance. Accordingly, the conventional expandable implanting device cannot be applied to treat and rectify bone tissue and structure.

Furthermore, the conventional expandable implanting device has the following disadvantages:

1. The threaded driving structure expands and retains spines poorly.

2. The threaded driving structure is complicated and is produced at high cost.

The present invention has arisen to mitigate and/or obviate the afore-described disadvantages.

SUMMARY OF THE INVENTION

The primary objective of the present invention is to provide an expandable implant of a minimally invasive surgery which has a symmetrical connecting structure to generate an expansion and to retain a bottom end of two sides of an implanted portion to treat and rectify bone tissue and structure.

To obtain the above and other objectives, an expandable implant of a minimally invasive surgery provided by the present invention contains a body, a positioning post, two first connecting sets, two second connecting sets, and two expanding pieces.

Thereby, the expandable implant of the minimally invasive surgery has the following advantages:

1. The expandable implant has an expandable connecting structure to retain an implanted portion of spines effectively.

2. The expandable implant is inserted and placed into a tiny wound via tissue by ways of an implanting apparatus.

3. The expandable implant is operated easily in a minimally invasive surgery.

4. The expandable implant is removed and replaced quickly.

5. The expandable implant has a simplified structure and a stable balance.

DETAILED DESCRIPTION OF THE PREFERRED EMBODIMENTS

The present invention will be clearer from the following description when viewed together with the accompanying drawings, which show, for purpose of illustration only, the preferred embodiments in accordance with the present invention.

Figure 1:
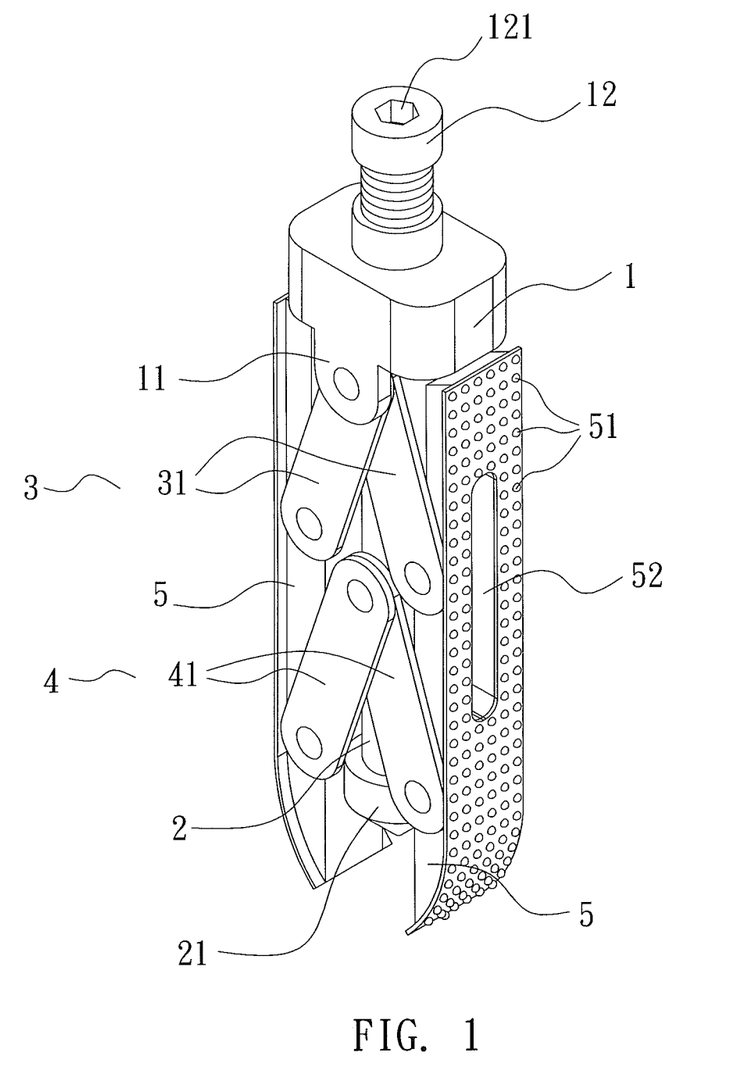
FIG. 1 is a perspective view of the assembly of an expandable implant of a minimally invasive surgery according to a preferred embodiment of the present invention.
Figure 2:
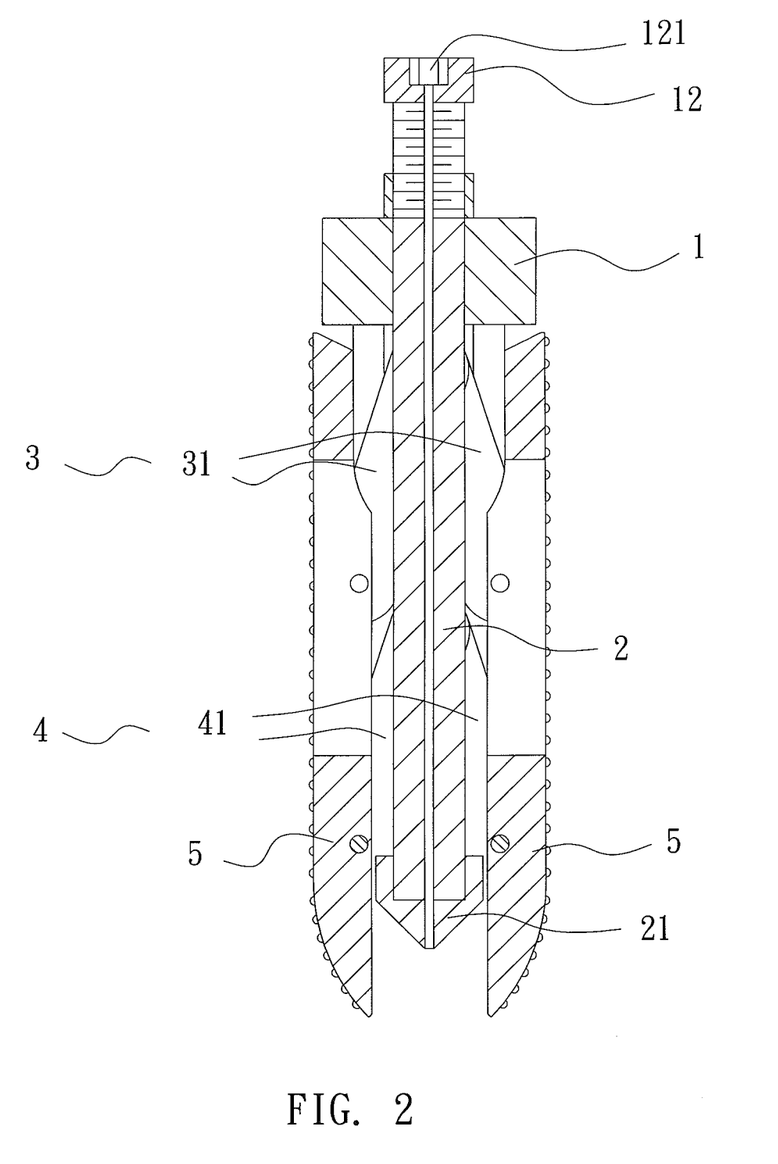
FIG. 2 is a cross sectional view of the assembly of the expandable implant of the minimally invasive surgery according to the preferred embodiment of the present invention.

With reference to FIGS. 1 and 2, an expandable implant of a minimally invasive surgery according to a preferred embodiment of the present invention comprises: a body 1, a positioning post 2, two first connecting sets 3, two second connecting sets 4, and two expanding pieces 5.

The body 1 includes two seats 11, and an adjusting knob 12 fixed on the two seats 11, and the adjusting knob 12 has a hexagonal hole 121 defined therein.

The positioning post 2 inserts into the body 1 and includes one side contacting with the adjusting knob 12 and another side having a conical member 21.

The two first connecting sets 3 axially couple with the two seats 11 of the body 1, and each first connecting set 3 has two first rods 31 coupling with a respective one of the two seats 11 of the body 1.

The two second connecting sets 4 axially connect with two sides of a middle section of the positioning post 2, and each second connecting set 4 has two second rods 41 coupling with the positioning post 2.

A side of a middle section of each expanding piece 5 axially connects with one of the two first rods 31 of each first connecting set 3, and a side of a bottom end of each expanding piece 5 axially couples with one of the two second rods 41 of each second connecting set 4.

Each expanding piece 5 includes a plurality of bosses 51 arranged on an outer surface thereof and a slot 52 defined thereon.

Figure 3:
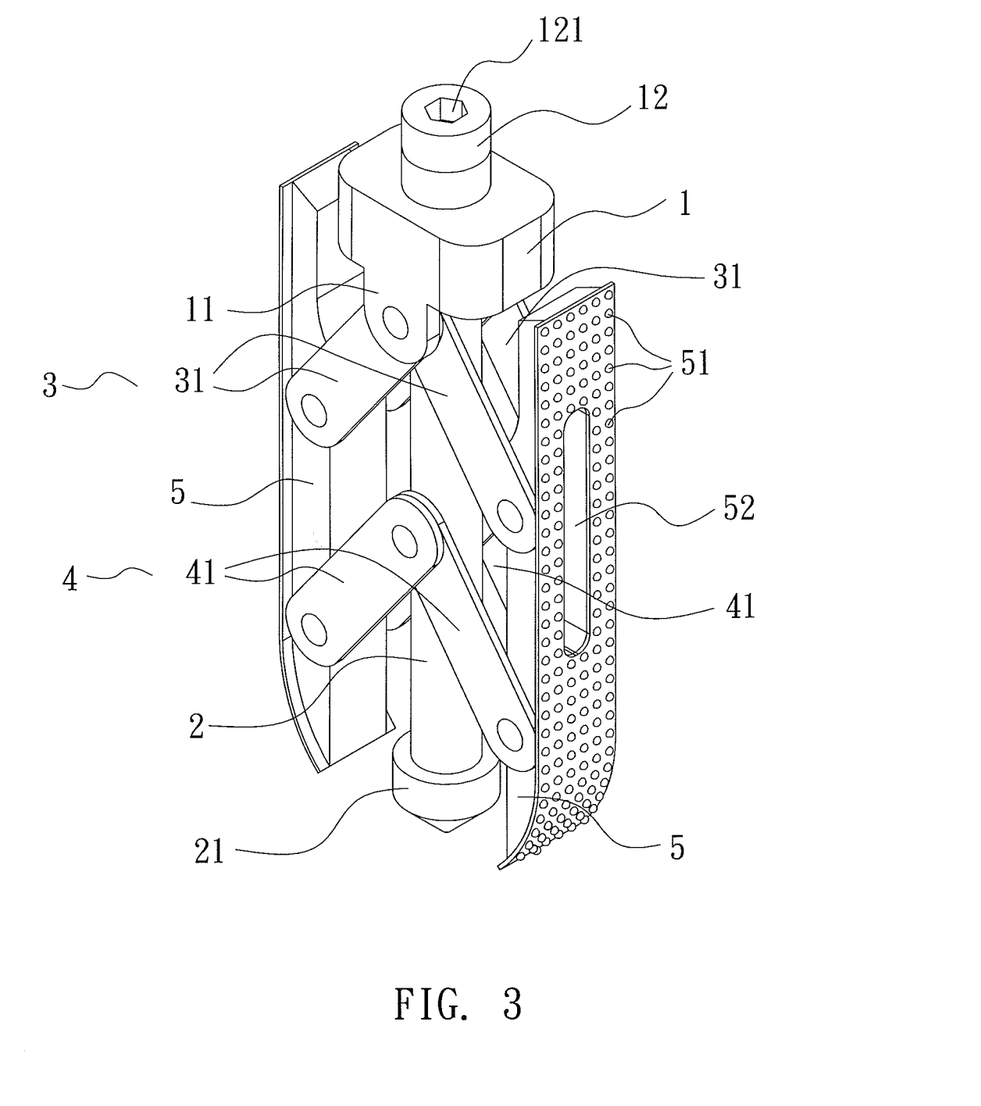
FIG. 3 is another perspective view of the assembly of the expandable implant of the minimally invasive surgery according to the preferred embodiment of the present invention.
Figure 4:
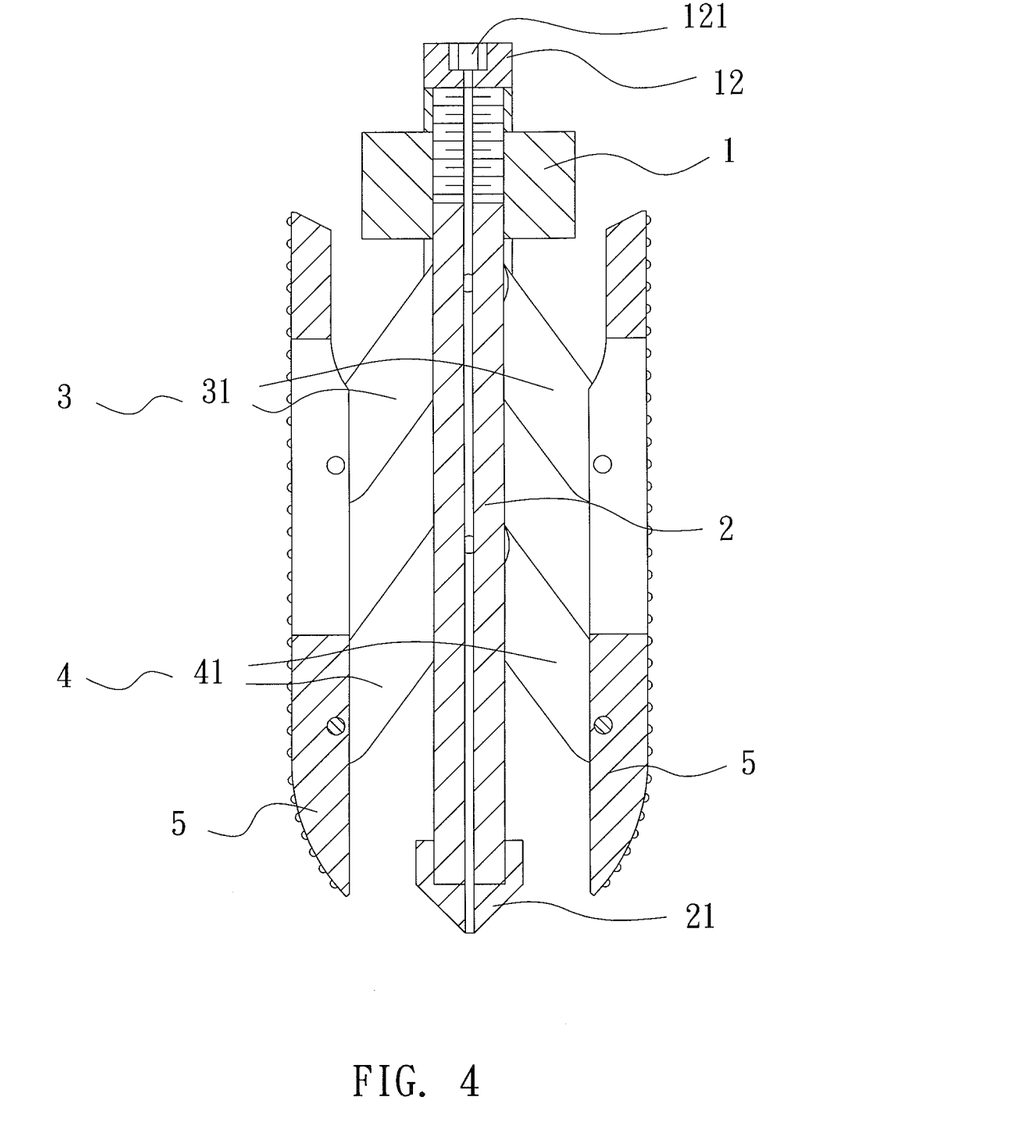
FIG. 4 is another cross sectional view of the assembly of the expandable implant of the minimally invasive surgery according to the preferred embodiment of the present invention.
Figure 5:
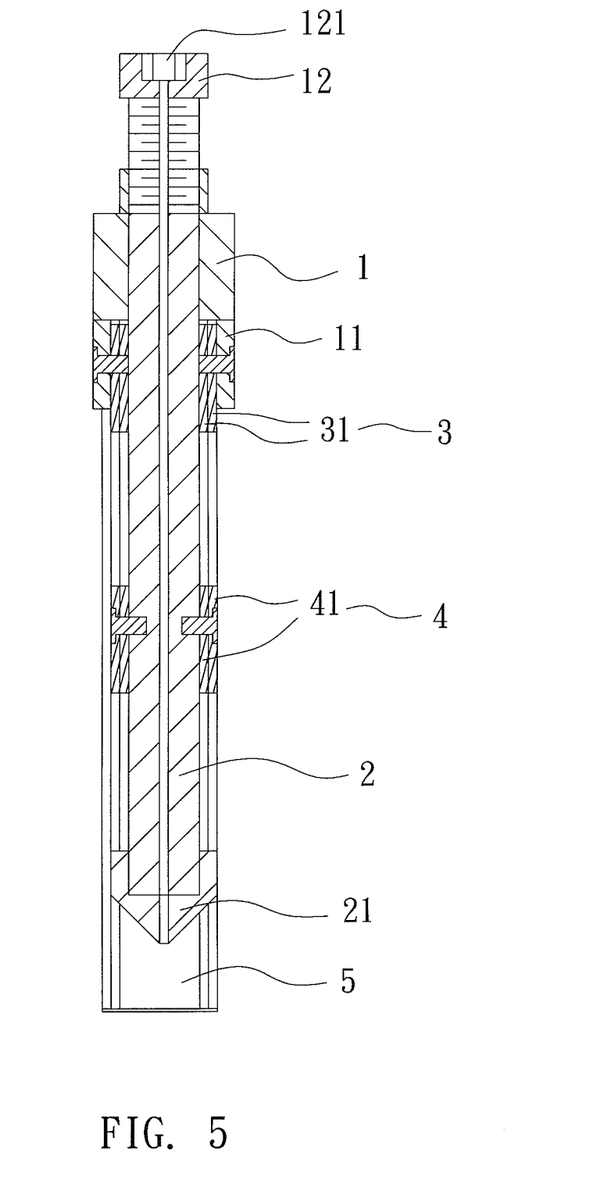
FIG. 5 is also another cross sectional view of the assembly of the expandable implant of the minimally invasive surgery according to the preferred embodiment of the present invention.

Referring to FIGS. 3, 4 and 5, when the adjusting knob 12 of the body 1 is rotated downwardly, the positioning post 2 is pushed downwardly to drive four second rods 41 of the two second connecting sets 4 to expand outward, and the two expanding pieces 5 expand outward simultaneously so that four first rods 31 of the two first connecting sets 3 expand outwardly to expand the two expanding pieces 5 as well. Accordingly, the two first connecting sets 3 and the two second connecting sets 4 are applied to expand the two expanding pieces 5 stably and evenly, thus implanting an implant securely.

Figure 6:
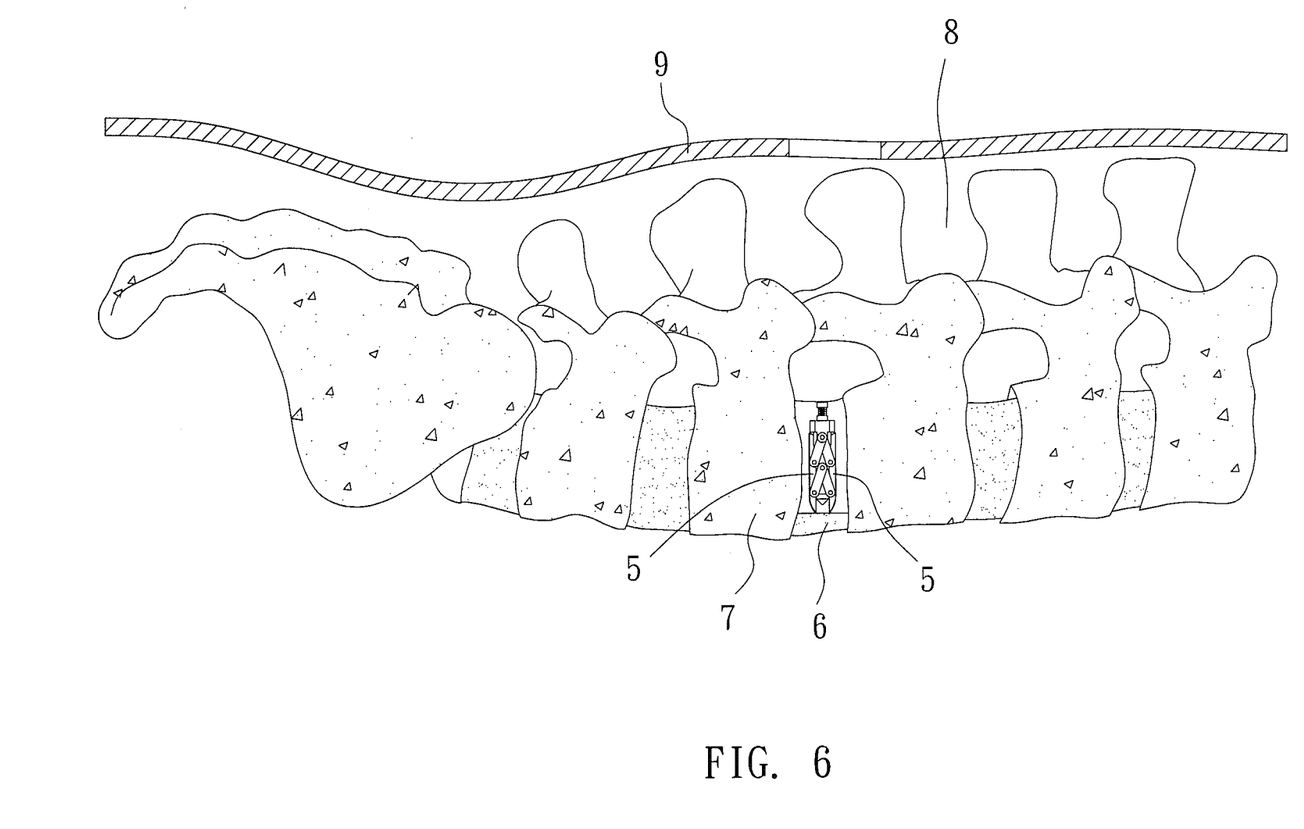
FIG. 6 is a cross sectional view of the operation of the expandable implant of the minimally invasive surgery according to the preferred embodiment of the present invention.

As shown in FIG. 6, the expandable implant, which comprises the two expanding pieces 5, is implanted into a spine 7 of a muscle tissue 8 via skin 9 by ways of a medical apparatus.

Figure 7:
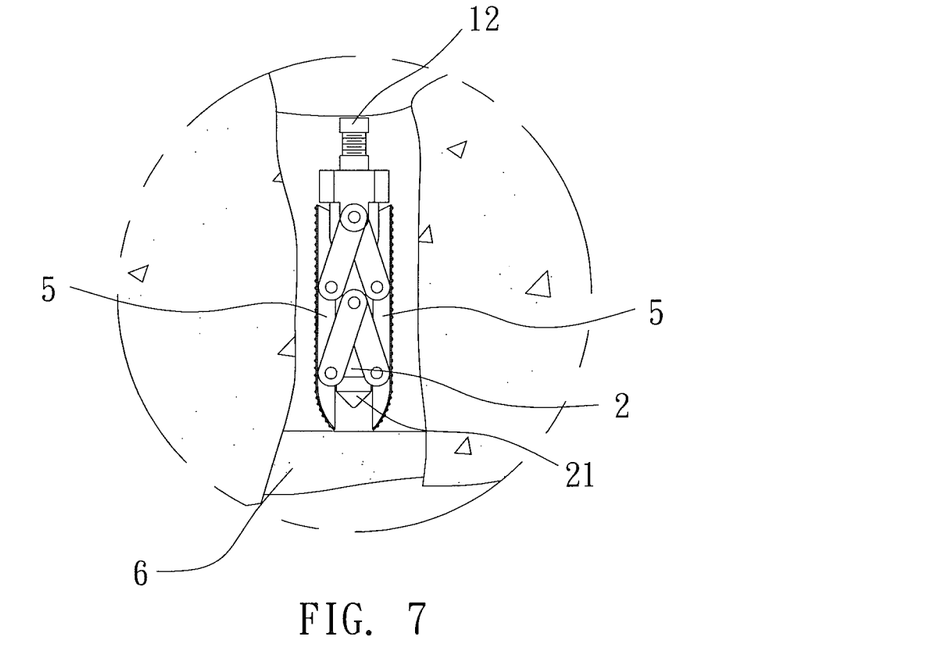
FIG. 7 is an amplified diagram showing a part of an application of the expandable implant of the minimally invasive surgery according to the preferred embodiment of the present invention.
Figure 8:
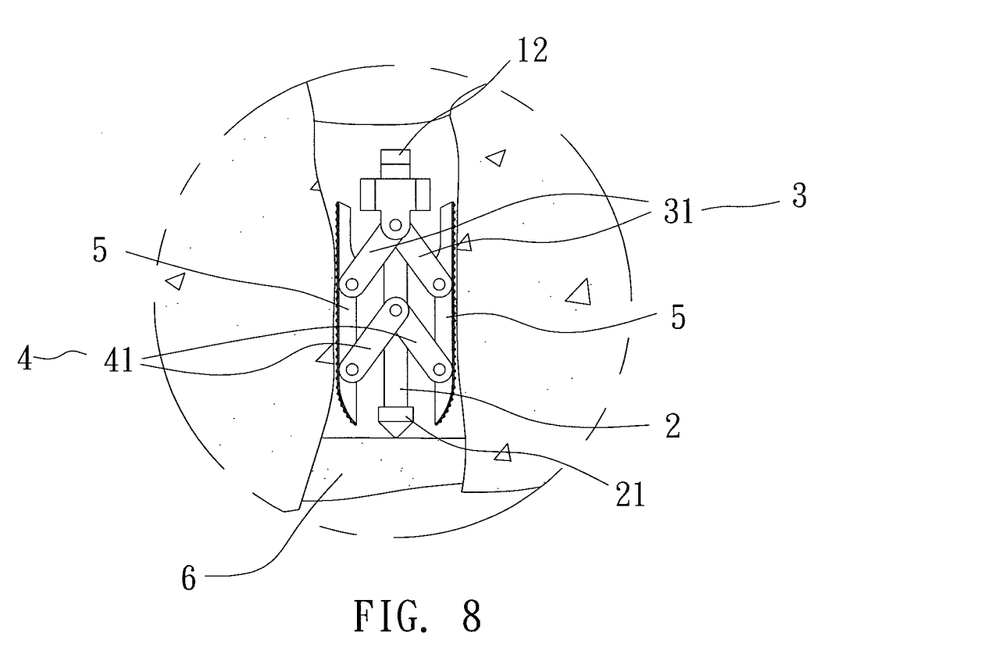
FIG. 8 is another amplified diagram showing a part of the application of the expandable implant of the minimally invasive surgery according to the preferred embodiment of the present invention.

As illustrated in FIGS. 7 and 8, in an application of the expandable implant, when the expandable implant, which comprises the two expanding pieces 5, is implanted into a cartilage tissue 6. The adjusting knob 12 is not rotated downward, so the positioning post 2 is located at an original position, and the two expanding pieces 5 are in a retracting state. As shown in FIG. 7, when the adjusting knob 12 is rotated downwardly, the positioning post 2 moves downwardly to retain a bottom end of a desired implanted portion of the cartilage tissue 6, such that the four second rods 41 of the two second connecting sets 4 are driven to actuate the two expanding pieces 5 to expand outward. Hence, the two expanding pieces 5 retain two side walls of the implanted portion of the cartilage tissue 6, and the four first rods 31 of the two first connecting sets 3 keep expansion evenly and stably as illustrated in FIG. 8.

Figure 9:
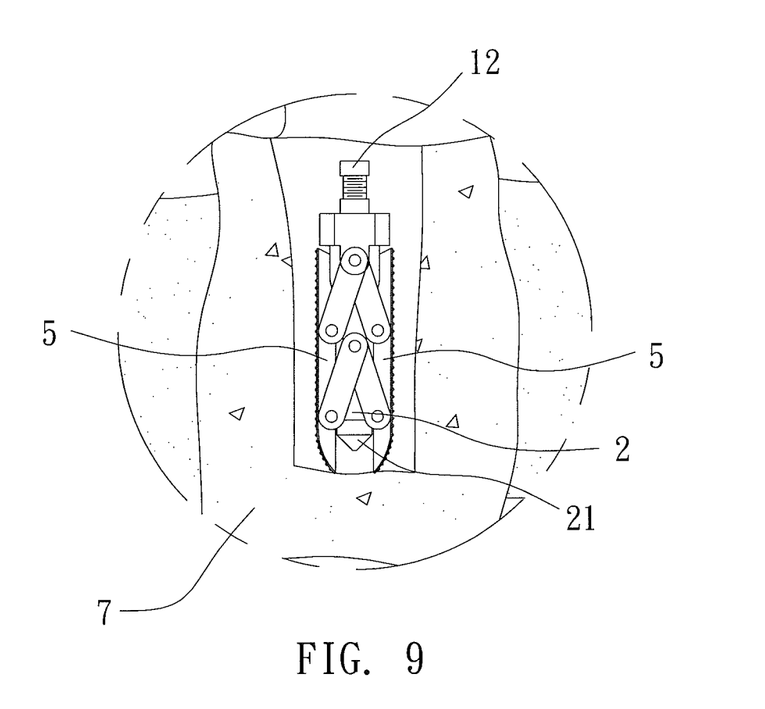
FIG. 9 is an amplified diagram showing a part of another application of the expandable implant of the minimally invasive surgery according to the preferred embodiment of the present invention.
Figure 10:
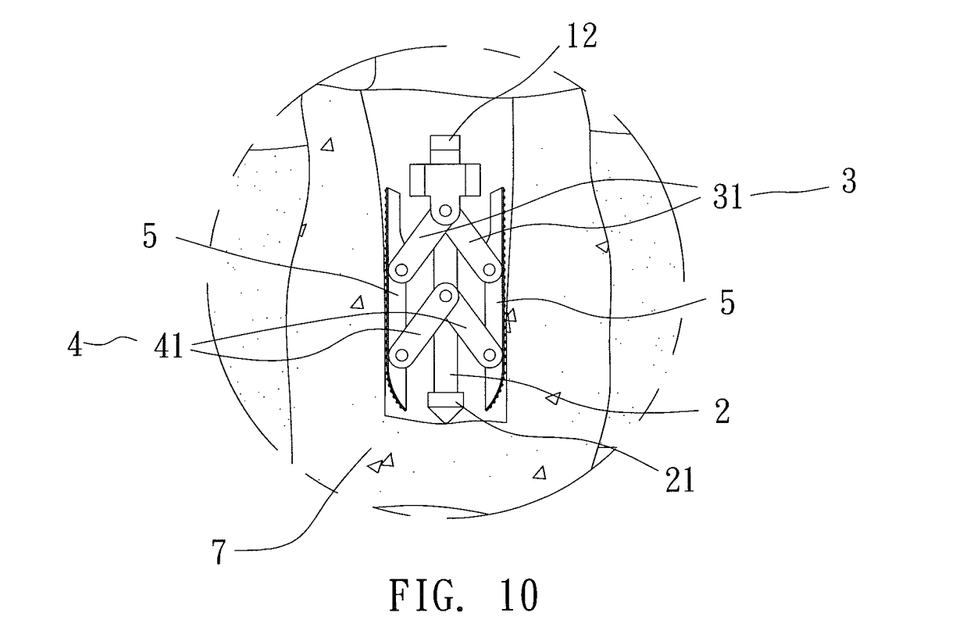
FIG. 10 is another amplified diagram showing a part of the another application of the expandable implant of the minimally invasive surgery according to the preferred embodiment of the present invention.

Referring further to FIGS. 9 and 10, in another application of the expandable implant, when the expandable implant, which comprises the two expanding pieces 5, is implanted into the spine 7, the adjusting knob 12 is not rotated downwardly. Thus, the positioning post 2 is located at the original position, and the two expanding pieces 5 are in the retracting state as illustrated in FIG. 9. When the adjusting knob 12 is rotated downwardly, the positioning post 2 moves downwardly to retain a desired implanted portion of a bottom end of the spine 7, such that the four second rods 41 of the two second connecting sets 4 are driven to arcuate the two expanding pieces 5 to expand outward. Hence, the two expanding pieces 5 retain two side walls of the implanted portion of the spine 7, and the four first rods 31 of the two first connecting sets 3 keep expansion evenly and stably as illustrated in FIG. 10.

Thereby, the expandable implant of the minimally invasive surgery of the present invention comprises the body 1, the positioning post 2, the two first connecting sets 3, the two second connecting sets 4, and the two expanding pieces 5 to obtain an expansion effect by ways of the two first connecting sets 3 and the two second connecting sets 4. Hence, the positioning post 2 and the two expanding pieces 5 retain the two side walls and the bottom end of the implanted portion to facilitate positioning of the implant, thus repairing bone tissue and reinforcing bone structure. Accordingly, the expandable implant of the minimally invasive surgery of the present invention is used to treat and rectify spines. Also, the expandable implant is served to decrease an area of a wound.

While various embodiments in accordance with the present invention have been shown and described, it is clear to those skilled in the art that further embodiments may be made without departing from the scope of the present invention.

What is claimed is:

1. An expandable implant of a minimally invasive surgery comprising:
   a body including two seats and an adjusting knob fixed on the two seats;
   a positioning post inserted into the body in an axial direction and including one side contacting with the adjusting knob and another side having a conical member;
   two first connecting sets coupling with the two seats of the body at a first location, with each first connecting set having two first rods coupling with a respective one of the two seats of the body;
   two second connecting sets connecting with two sides of a middle section of the positioning post at a second location, with each second connecting set having two second rods coupling with the positioning post; and
   two expanding pieces each having one side of a middle section connecting with one of the two first rods of each first connecting set at a third location and one side of a bottom end coupling with one of the two second rods of each second connecting set at a fourth location, with the third location located intermediate and spaced from the first location and the second location in the axial direction and with the second location located intermediate and spaced from the third location and the fourth location in the axial direction, with the positioning post being free of coupling between the second location and the conical member.

2. The expandable implant of the minimally invasive surgery as claimed in claim 1, wherein the adjusting knob has a hexagonal hole defined therein.

3. The expandable implant of the minimally invasive surgery as claimed in claim 1, wherein each expanding piece includes a plurality of spaced bosses arranged in an array of rows and columns on an outer surface thereof.

4. The expandable implant of the minimally invasive surgery as claimed in claim 1, wherein each expanding piece includes a slot defined thereon.

\* \* \* \* \*